(12) United States Patent
Toba et al.

(10) Patent No.: US 12,087,430 B2
(45) Date of Patent: Sep. 10, 2024

(54) INFORMATION PROCESSING APPARATUS, INFORMATION PROCESSING METHOD, AND NON-TRANSITORY STORAGE MEDIUM

(71) Applicant: CANON KABUSHIKI KAISHA, Tokyo (JP)

(72) Inventors: Shuhei Toba, Kanagawa (JP); Yoshinori Hirano, Chiba (JP)

(73) Assignee: Canon Kabushiki Kaisha, Tokyo (JP)

( * ) Notice: Subject to any disclaimer, the term of this patent is extended or adjusted under 35 U.S.C. 154(b) by 504 days.

(21) Appl. No.: 17/365,829

(22) Filed: Jul. 1, 2021

(65) Prior Publication Data
US 2022/0005589 A1 Jan. 6, 2022

(30) Foreign Application Priority Data
Jul. 3, 2020 (JP) .................. 2020-115381

(51) Int. Cl.
*G16H 30/40* (2018.01)
*G06N 5/04* (2023.01)
*G06T 7/00* (2017.01)

(52) U.S. Cl.
CPC .............. *G16H 30/40* (2018.01); *G06N 5/04* (2013.01); *G06T 7/0014* (2013.01); *G06T 2207/20081* (2013.01)

(58) Field of Classification Search
CPC . G06N 20/00; G06N 5/02; G06N 5/04; G06T 2207/20081; G06T 7/0014; G16H 30/20; G16H 30/40; G16H 50/20; G16H 50/70
See application file for complete search history.

(56) References Cited

U.S. PATENT DOCUMENTS

| | | | |
|---|---|---|---|
| 2019/0057314 A1* | 2/2019 | Julian | H04L 67/34 |
| 2019/0122073 A1* | 4/2019 | Ozdemir | G06V 20/56 |
| 2019/0200977 A1* | 7/2019 | Shelton, IV | A61B 17/02 |

(Continued)

FOREIGN PATENT DOCUMENTS

| | | |
|---|---|---|
| JP | H0512352 A | 1/1993 |
| JP | 2019129989 A | 8/2019 |

OTHER PUBLICATIONS

Justin Ker, "Deep Learning Applications in Medical Image Analysis," Mar. 13, 2018, IEEE Access, vol. 6, 2018, pp. 9375-9385.*

(Continued)

*Primary Examiner* — Omar S Ismail
(74) *Attorney, Agent, or Firm* — Canon U.S.A., Inc. IP Division

(57) ABSTRACT

An information processing apparatus includes an inference model information acquisition unit configured to acquire information about each inference model comprising a plurality of inference models, a supplementary information acquisition unit configured to acquire supplementary information supplement to medical image data that is an inference target acquired by imaging a test subject, and an inference model selection unit configured to select an inference model to be applied to the medical image data from the plurality of inference models based on the information about each of the inference models and the supplementary information, wherein the medical image data is an inference target.

11 Claims, 12 Drawing Sheets

(56) References Cited

U.S. PATENT DOCUMENTS

| | | | |
|---|---|---|---|
| 2019/0206565 A1* | 7/2019 | Shelton, IV | A61B 90/90 |
| 2019/0371433 A1* | 12/2019 | Wang | G16H 30/40 |
| 2019/0392547 A1* | 12/2019 | Katouzian | G06V 20/62 |
| 2020/0227160 A1* | 7/2020 | Youngblood | G16H 40/20 |
| 2020/0323464 A1* | 10/2020 | Rapaka | G16H 10/20 |
| 2021/0042577 A1* | 2/2021 | Martin | G06F 18/214 |
| 2021/0158525 A1* | 5/2021 | Iwase | A61B 3/0025 |
| 2021/0202072 A1* | 7/2021 | Yi | G16H 50/20 |
| 2021/0304402 A1* | 9/2021 | Morgas | G06T 7/12 |
| 2021/0397254 A1* | 12/2021 | Seibel | G06N 3/08 |

OTHER PUBLICATIONS

M.R. Avendi , "A combined deep-learning and deformable-model approach to fully automatic segmentation of the left ventricle in cardiac MRI," Feb. 6, 2016, Medical Image Analysis 30 (2016) ,pp. 110-117.*

* cited by examiner

FIG. 4A
SUPPLEMENTARY INFORMATION OF MEDICAL IMAGE DATA THAT IS INFERENCE TARGET

APPARATUS TYPE: CT
IMAGING REGION: CHEST REGION
CONTRAST MEDIUM: NO
SLICE THICKNESS: 1.0 mm

FIG. 4B
INFORMATION ABOUT INFERENCE MODEL

INFERENCE MODEL 1
TARGET DISEASE NAME: PNEUMOTHORAX
APPARATUS TYPE: CR
IMAGING REGION: CHEST REGION
CONTRAST MEDIUM: NO
SLICE THICKNESS: —

INFERENCE MODEL 2
TARGET DISEASE NAME: PNEUMOTHORAX
APPARATUS TYPE: CT
IMAGING REGION: CHEST REGION
CONTRAST MEDIUM: NO
SLICE THICKNESS: 3.0 mm

INFERENCE MODEL 3
TARGET DISEASE NAME: CEREBRAL INFARCTION
APPARATUS TYPE: MRI
IMAGING REGION: HEAD REGION
CONTRAST MEDIUM: NO
SLICE THICKNESS: 1.5 mm

INFERENCE MODEL 4
TARGET DISEASE NAME: LUNG NODULE
APPARATUS TYPE: CT
IMAGING REGION: CHEST REGION
CONTRAST MEDIUM: NO
SLICE THICKNESS: 1.0 mm

INFERENCE MODEL 5
TARGET DISEASE NAME: AORTIC DISSECTION
APPARATUS TYPE: CT
IMAGING REGION: THORACOABDOMINAL REGION
CONTRAST MEDIUM: NO
SLICE THICKNESS: 3.0 mm

INFERENCE MODEL 6
TARGET DISEASE NAME: INTRACRANIAL BLEEDING
APPARATUS TYPE: MRI
IMAGING REGION: HEAD REGION
CONTRAST MEDIUM: YES
SLICE THICKNESS: 2.0 mm

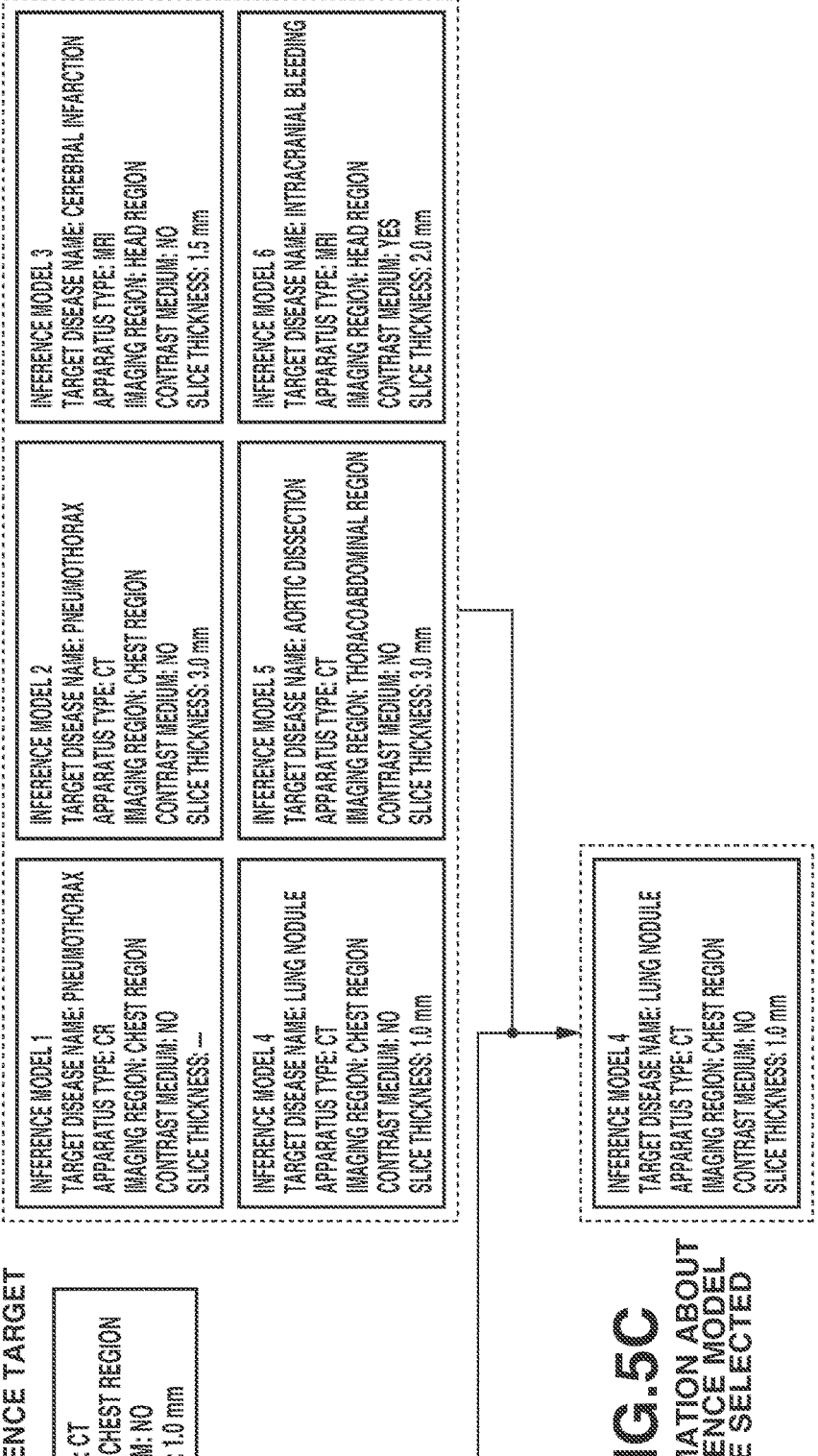

FIG.6

| IMAGING REGION OF INFERENCE MODEL \ IMAGING REGION OF MEDICAL IMAGE THAT IS INFERENCE TARGET | HEAD REGION | CERVICAL REGION | CHEST REGION | ABDOMINAL REGION | PELVIC REGION | FOUR LIMBS | HEAD AND NECK REGION | THORACOABDOMINAL REGION |
|---|---|---|---|---|---|---|---|---|
| HEAD REGION | ○ | | | | | | ○ | |
| CERVICAL REGION | | ○ | | | | | ○ | |
| CHEST REGION | | | ○ | | | | | ○ |
| ABDOMINAL REGION | | | | ○ | | | | ○ |
| PELVIC REGION | | | | | ○ | | | |
| FOUR LIMBS | | | | | | ○ | | |
| HEAD AND NECK REGION | ○ | ○ | | | | | ○ | |
| THORACOABDOMINAL REGION | | | ○ | ○ | | | | ○ |

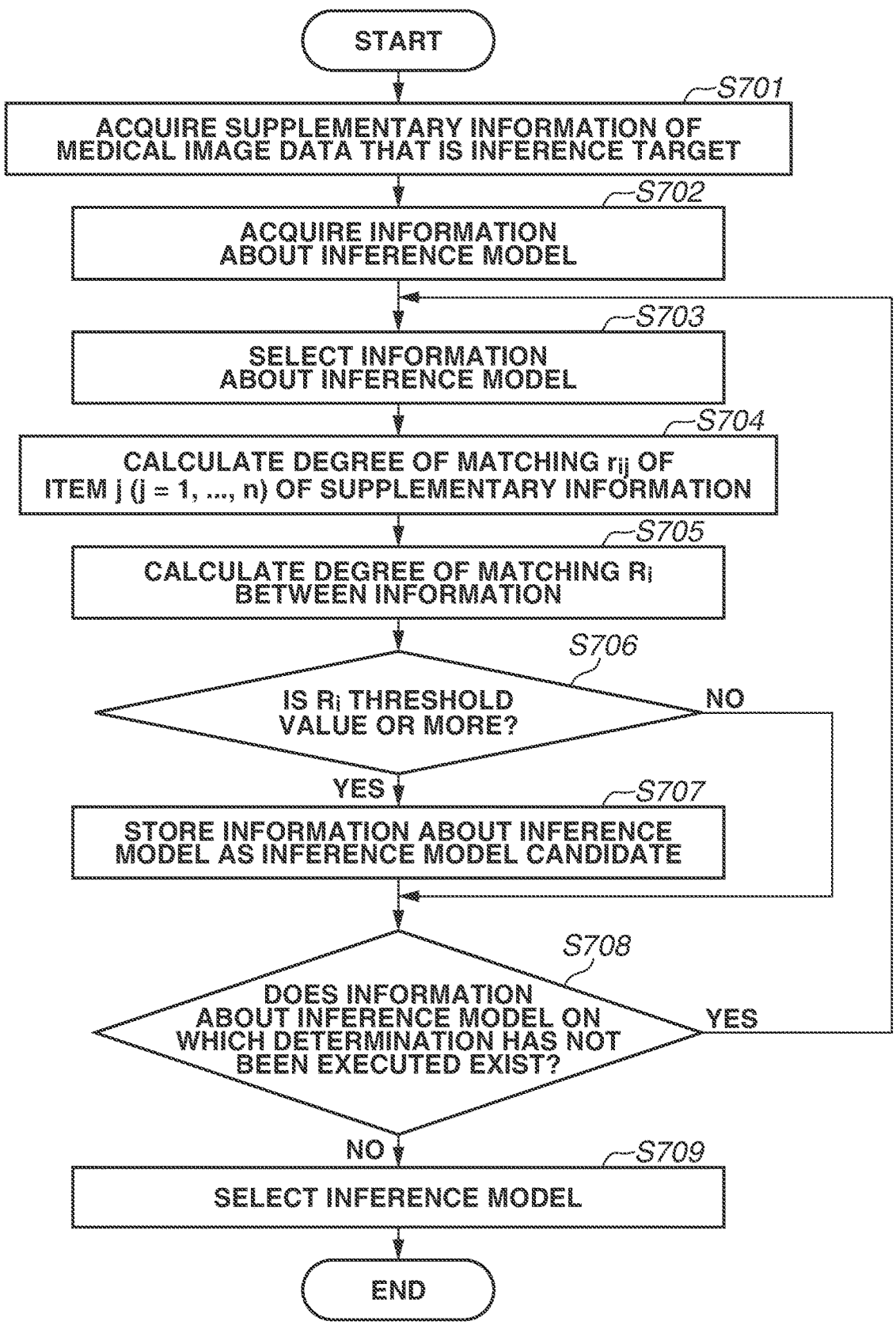

FIG. 8A
SUPPLEMENTARY INFORMATION OF MEDICAL IMAGE DATA THAT IS INFERENCE TARGET

APPARATUS TYPE: CT
IMAGING REGION: CHEST REGION
CONTRAST MEDIUM: NO
SLICE THICKNESS: 1.0 mm

FIG. 8B
INFORMATION ABOUT INFERENCE MODEL

INFERENCE MODEL 1
TARGET DISEASE NAME: PNEUMOTHORAX
APPARATUS TYPE: CR
IMAGING REGION: CHEST REGION
CONTRAST MEDIUM: NO
SLICE THICKNESS: —

INFERENCE MODEL 2
TARGET DISEASE NAME: PNEUMOTHORAX
APPARATUS TYPE: CT
IMAGING REGION: CHEST REGION
CONTRAST MEDIUM: NO
SLICE THICKNESS: 3.0 mm

INFERENCE MODEL 3
TARGET DISEASE NAME: CEREBRAL INFARCTION
APPARATUS TYPE: MRI
IMAGING REGION: HEAD REGION
CONTRAST MEDIUM: NO
SLICE THICKNESS: 1.5 mm

INFERENCE MODEL 4
TARGET DISEASE NAME: LUNG NODULE
APPARATUS TYPE: CT
IMAGING REGION: CHEST REGION
CONTRAST MEDIUM: NO
SLICE THICKNESS: 1.0 mm

INFERENCE MODEL 5
TARGET DISEASE NAME: AORTIC DISSECTION
APPARATUS TYPE: CT
IMAGING REGION: THORACOABDOMINAL REGION
CONTRAST MEDIUM: NO
SLICE THICKNESS: 3.0 mm

INFERENCE MODEL 6
TARGET DISEASE NAME: INTRACRANIAL BLEEDING
APPARATUS TYPE: MRI
IMAGING REGION: HEAD REGION
CONTRAST MEDIUM: YES
SLICE THICKNESS: 2.0 mm

FIG. 8C
DEGREE OF MATCHING OF EACH ITEM

INFERENCE MODEL 1
APPARATUS TYPE: 0
IMAGING REGION: 1
CONTRAST MEDIUM: 1
SLICE THICKNESS: 0.0

INFERENCE MODEL 2
APPARATUS TYPE: 1
IMAGING REGION: 1
CONTRAST MEDIUM: 1
SLICE THICKNESS: 0.0

INFERENCE MODEL 3
APPARATUS TYPE: 0
IMAGING REGION: 0
CONTRAST MEDIUM: 1
SLICE THICKNESS: 0.75

INFERENCE MODEL 4
APPARATUS TYPE: 1
IMAGING REGION: 1
CONTRAST MEDIUM: 1
SLICE THICKNESS: 1.0

INFERENCE MODEL 5
APPARATUS TYPE: 1
IMAGING REGION: 0
CONTRAST MEDIUM: 1
SLICE THICKNESS: 0.0

INFERENCE MODEL 6
APPARATUS TYPE: 0
IMAGING REGION: 0
CONTRAST MEDIUM: 0
SLICE THICKNESS: 0.5

FIG. 8D
TOTAL DEGREE OF MATCHING OF INFORMATION

| INFERENCE MODEL 1 | INFERENCE MODEL 2 | INFERENCE MODEL 3 |
|---|---|---|
| 0.2500 | 0.7500 | 0.4375 |

| INFERENCE MODEL 4 | INFERENCE MODEL 5 | INFERENCE MODEL 6 |
|---|---|---|
| 1.0000 | 0.2500 | 0.1250 |

FIG. 9A
SUPPLEMENTARY INFORMATION OF MEDICAL IMAGE DATA THAT IS INFERENCE TARGET

APPARATUS TYPE: CT
IMAGING REGION: CHEST REGION
CONTRAST MEDIUM: NO
SLICE THICKNESS: 1.0 mm

FIG. 9B
INFORMATION ABOUT INFERENCE MODEL

INFERENCE MODEL 1
TARGET DISEASE NAME: PNEUMOTHORAX
APPARATUS TYPE: CR
IMAGING REGION: CHEST REGION
CONTRAST MEDIUM: NO
SLICE THICKNESS: —

INFERENCE MODEL 2
TARGET DISEASE NAME: PNEUMOTHORAX
APPARATUS TYPE: CT
IMAGING REGION: CHEST REGION
CONTRAST MEDIUM: NO
SLICE THICKNESS: 3.0 mm

INFERENCE MODEL 3
TARGET DISEASE NAME: CEREBRAL INFARCTION
APPARATUS TYPE: MRI
IMAGING REGION: HEAD REGION
CONTRAST MEDIUM: NO
SLICE THICKNESS: 1.5 mm

INFERENCE MODEL 4
TARGET DISEASE NAME: LUNG NODULE
APPARATUS TYPE: CT
IMAGING REGION: CHEST REGION
CONTRAST MEDIUM: NO
SLICE THICKNESS: 1.0 mm

INFERENCE MODEL 5
TARGET DISEASE NAME: AORTIC DISSECTION
APPARATUS TYPE: CT
IMAGING REGION: THORACOABDOMINAL REGION
CONTRAST MEDIUM: NO
SLICE THICKNESS: 3.0 mm

INFERENCE MODEL 6
TARGET DISEASE NAME: INTRACRANIAL BLEEDING
APPARATUS TYPE: MRI
IMAGING REGION: HEAD REGION
CONTRAST MEDIUM: YES
SLICE THICKNESS: 2.0 mm

FIG. 9C
DEGREE OF MATCHING OF EACH ITEM

INFERENCE MODEL 1
APPARATUS TYPE: 0
IMAGING REGION: 1
CONTRAST MEDIUM: 1
SLICE THICKNESS: 0.0

INFERENCE MODEL 2
APPARATUS TYPE: 1
IMAGING REGION: 1
CONTRAST MEDIUM: 1
SLICE THICKNESS: 0.0

INFERENCE MODEL 3
APPARATUS TYPE: 0
IMAGING REGION: 0
CONTRAST MEDIUM: 1
SLICE THICKNESS: 0.75

INFERENCE MODEL 4
APPARATUS TYPE: 1
IMAGING REGION: 1
CONTRAST MEDIUM: 1
SLICE THICKNESS: 1.0

INFERENCE MODEL 5
APPARATUS TYPE: 1
IMAGING REGION: 0
CONTRAST MEDIUM: 1
SLICE THICKNESS: 0.0

INFERENCE MODEL 6
APPARATUS TYPE: 0
IMAGING REGION: 0
CONTRAST MEDIUM: 0
SLICE THICKNESS: 0.5

FIG. 9D
WEIGHT OF EACH ITEM

APPARATUS TYPE: 0.5
IMAGING REGION: 0.2
CONTRAST MEDIUM: 0.2
SLICE THICKNESS: 0.1

FIG. 9E
TOTAL DEGREE OF MATCHING OF INFORMATION

| INFERENCE MODEL 1 | INFERENCE MODEL 2 | INFERENCE MODEL 3 |
|---|---|---|
| 0.400 | 0.900 | 0.275 |

| INFERENCE MODEL 4 | INFERENCE MODEL 5 | INFERENCE MODEL 6 |
|---|---|---|
| 1.000 | 0.700 | 0.05 |

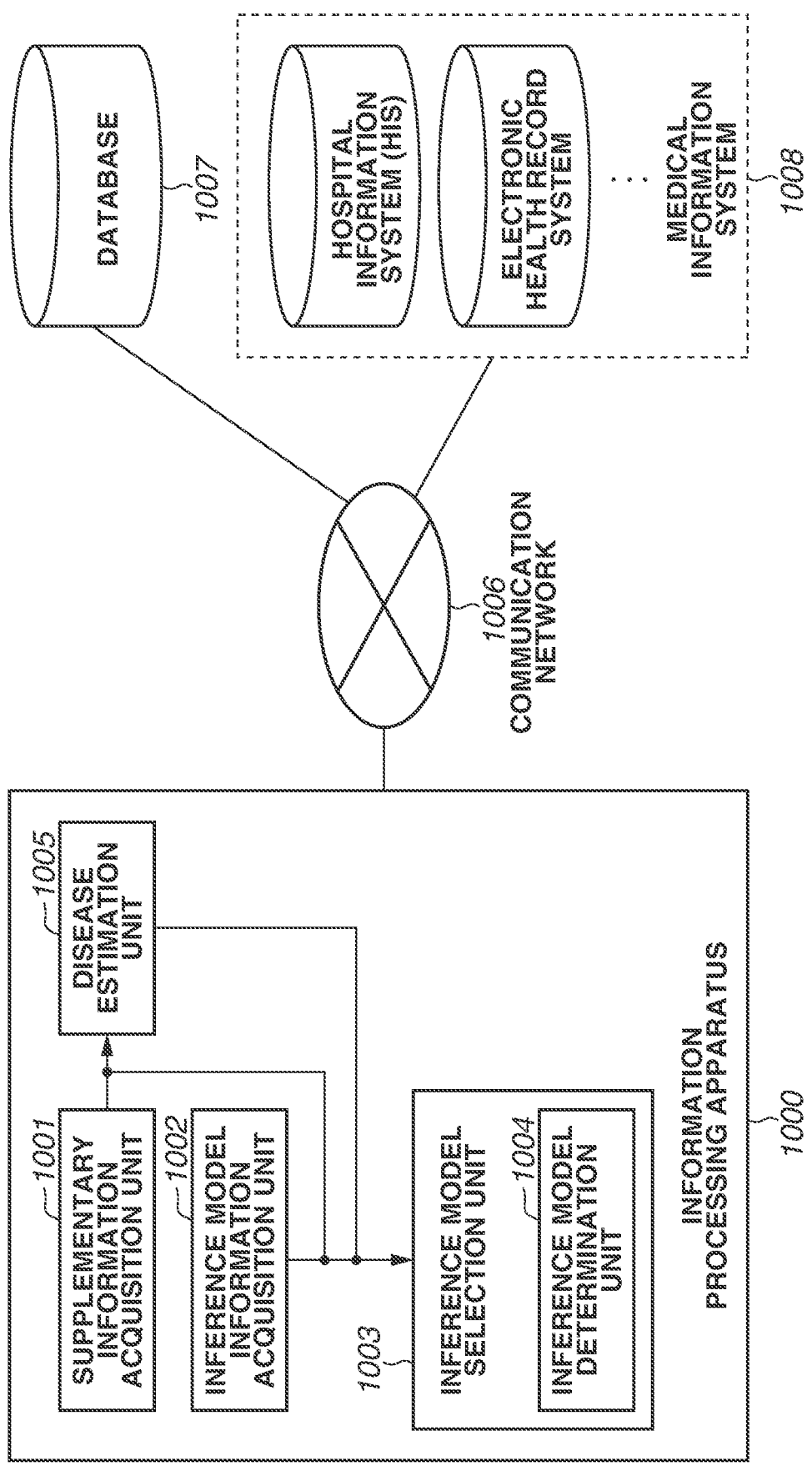

FIG. 12A

SUPPLEMENTARY INFORMATION OF MEDICAL IMAGE DATA THAT IS INFERENCE TARGET

TARGET DISEASE NAME: PNEUMOTHORAX, AORTIC DISSECTION
APPARATUS TYPE: CT
IMAGING REGION: CHEST REGION
CONTRAST MEDIUM: NO
SLICE THICKNESS: 1.0 mm

FIG. 12B

INFORMATION ABOUT INFERENCE MODEL

INFERENCE MODEL 1
TARGET DISEASE NAME: PNEUMOTHORAX
APPARATUS TYPE: CR
IMAGING REGION: CHEST REGION
CONTRAST MEDIUM: NO
SLICE THICKNESS: —

INFERENCE MODEL 2
TARGET DISEASE NAME: PNEUMOTHORAX
APPARATUS TYPE: CT
IMAGING REGION: CHEST REGION
CONTRAST MEDIUM: NO
SLICE THICKNESS: 3.0 mm

INFERENCE MODEL 3
TARGET DISEASE NAME: CEREBRAL INFARCTION
APPARATUS TYPE: MRI
IMAGING REGION: HEAD REGION
CONTRAST MEDIUM: NO
SLICE THICKNESS: 1.5 mm

INFERENCE MODEL 4
TARGET DISEASE NAME: LUNG NODULE
APPARATUS TYPE: CT
IMAGING REGION: CHEST REGION
CONTRAST MEDIUM: NO
SLICE THICKNESS: 1.0 mm

INFERENCE MODEL 5
TARGET DISEASE NAME: AORTIC DISSECTION
APPARATUS TYPE: CT
IMAGING REGION: THORACOABDOMINAL REGION
CONTRAST MEDIUM: NO
SLICE THICKNESS: 3.0 mm

INFERENCE MODEL 6
TARGET DISEASE NAME: INTRACRANIAL BLEEDING
APPARATUS TYPE: MRI
IMAGING REGION: HEAD REGION
CONTRAST MEDIUM: YES
SLICE THICKNESS: 2.0 mm

INFORMATION PROCESSING APPARATUS, INFORMATION PROCESSING METHOD, AND NON-TRANSITORY STORAGE MEDIUM

BACKGROUND

Field of the Disclosure

The present disclosure relates to an information processing apparatus which selects an appropriate inference model from a plurality of inference models based on supplementary information supplement to medical image data that is an inference target, an information processing method, and a non-transitory storage medium.

Description of the Related Art

With the development in an artificial intelligent technique including machine learning, a plurality of inference models which perform inference about a disease is provided on a platform such as a medical cloud service or a workstation for processing medical image data, and a user can receive an inference result by inputting medical image data that is an inference target to a desired inference model. It is often the case that medical image data used for training the inference model vary depending on a disease (e.g., pneumothorax, lung nodule, or cerebral infraction) that is an inference target and a type of medical image data based on a type of imaging apparatus or an imaging region.

In many cases, the user selects an inference model to be applied to medical image data that is an inference target, and inputs the medical image data to the selected inference model to execute inference processing. As a matter of course, the user can apply a plurality of inference models thereto without selecting an inference model. In that case, however, the processing efficiency will be low because the inference models are trained under different conditions, and thus the user has to check medical image data to be input thereto depending on the inference models and has to determine an appropriate result from a plurality of inference results obtained by the plurality of inference models. Thus, there has been an increasing demand for a method of selecting an inference model appropriate for medical image data that is an inference target while saving time and effort of the user.

Herein, a technique for determining whether medical image data input to an image data processing apparatus is a processing target (i.e., data appropriate for the processing) has been known. For example, a technique of acquiring supplementary information about medical image data and determining whether the medical image data is a processing target appropriate for temporal subtraction processing has been discussed in Japanese Patent Application Laid-Open No. 2019-0129989.

SUMMARY

By the technique discussed in Japanese Patent Application Laid-Open No. 2019-0129989, it is not possible to select an inference model appropriate for medical image data that is an inference target from a plurality of inference models.

Therefore, the present disclosure is directed to a technique of selecting an inference model appropriate for medical image data that is an inference target from a plurality of inference models while reducing time and effort of the user.

According to an aspect of the present invention, an information processing apparatus includes an inference model information acquisition unit configured to acquire information about each inference model comprising a plurality of inference models, a supplementary information acquisition unit configured to acquire supplementary information supplement to medical image data that is an inference target acquired by imaging a test subject, and an inference model selection unit configured to select an inference model to be applied to the medical image data from the plurality of inference models based on the information about each of the inference models and the supplementary information, wherein the medical image data is an inference target.

Further features of the present invention will become apparent from the following description of exemplary embodiments with reference to the attached drawings.

BRIEF DESCRIPTION OF THE DRAWINGS

FIGS. 4A and 4B are diagrams illustrating an example of information acquired in the first exemplary embodiment.

FIGS. 5A, 5B, and 5C are diagrams illustrating an example of a selection result of an inference model according to the first exemplary embodiment.

FIG. 6 is a table illustrating an example of a map representing whether information about an inference model matches supplementary information.

FIG. 7 is a flowchart illustrating processing according to a second exemplary embodiment.

FIGS. 8A, 8B, 8C, and 8D are diagrams illustrating an example of a calculation result of a degree of matching for each inference model according to the second exemplary embodiment.

FIGS. 9A, 9B, 9C, 9D, and 9E are diagrams illustrating an example of a calculation result of a degree of matching for each inference model according to a third exemplary embodiment.

FIG. 10 is a block diagram illustrating an information processing apparatus according to a fourth exemplary embodiment.

FIGS. 12A and 12B are diagrams illustrating an example of information acquired as a result of the processing in step S1104 in FIG. 11

DESCRIPTION OF THE EMBODIMENTS

Figure 1:
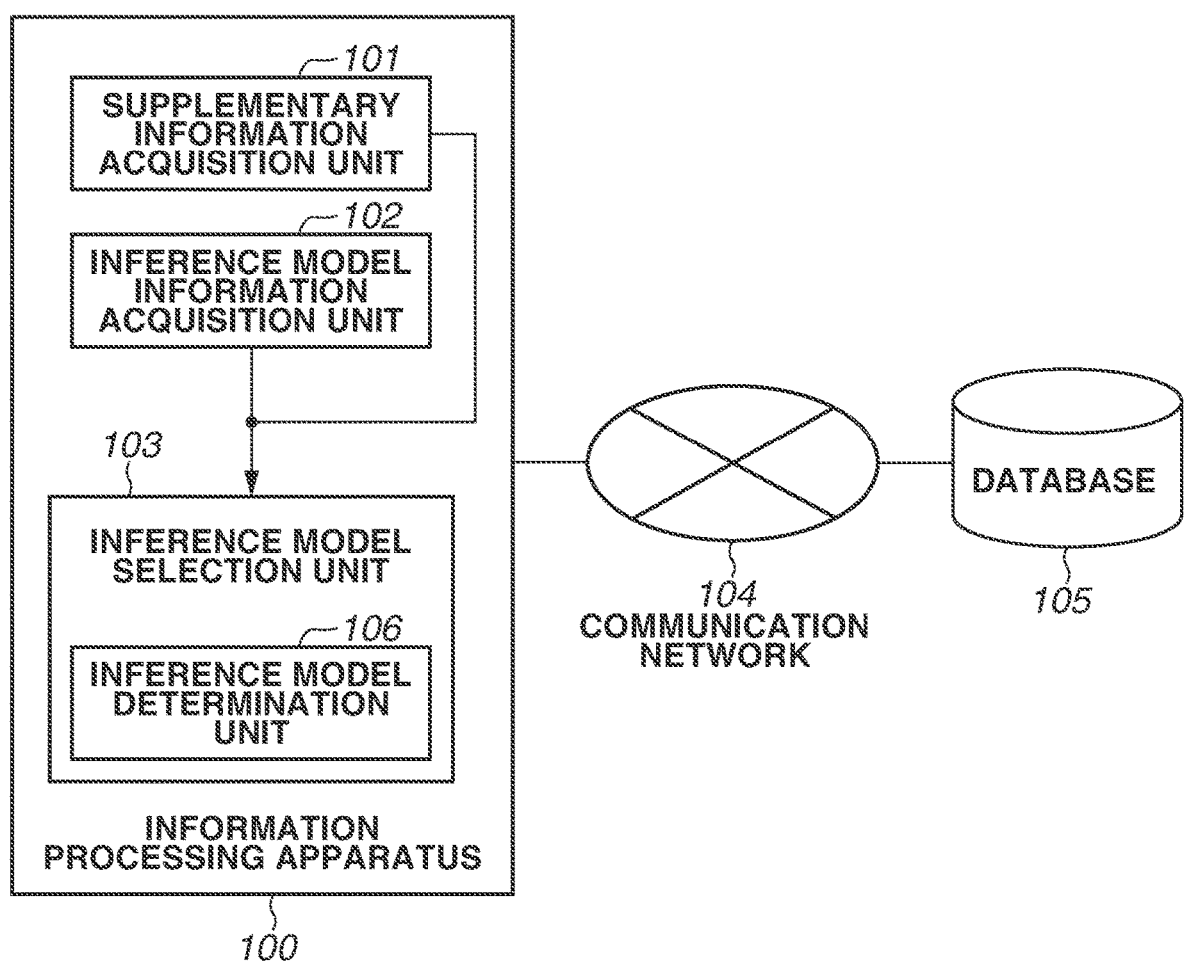
FIG. 1 is a block diagram illustrating a configuration of an information processing apparatus according to a first exemplary embodiment.

Hereinafter, exemplary embodiments for carrying out the present invention will be described with reference to the appended drawings. However, the present invention is not limited to examples illustrated in the drawings.

In a first exemplary embodiment, an information processing apparatus checks each item which constitutes supplementary information supplement to medical image data that is an inference target against each item which constitutes information about each of inference models that constitute a plurality of inference models to determine whether the items match each other. Then, based on the determination result, the information processing apparatus selects an inference model appropriate for the medical image data that is an inference target from the plurality of inference models. Hereinafter, the present exemplary embodiment will be described with reference to the drawings.

First, a configuration of the information processing apparatus according to the present invention will be described with reference to FIG. 1.

As illustrated in FIG. 1, an information processing apparatus 100 includes an supplementary information acquisition unit 101 which acquires supplementary information supplement to medical image data that is an inference target, an inference model information acquisition unit 102 which acquires information about each of inference models constituting a plurality of inference models that perform inference about a predetermined disease, and an inference model selection unit 103 which selects an inference model to be applied to medical image data that is an inference target from a plurality of inference models based on the supplementary information and the information about the inference model. The inference model selection unit 103 further includes an inference model determination unit 106 which determines whether the supplementary information conforms to the information about the inference model. Further, the information processing apparatus 100 is connected to a database 105 via a communication network 104. Hereinafter, each of the units will be described in detail.

The supplementary information acquisition unit 101 acquires various types of information (hereinafter, referred to as supplementary information) supplement to medical image data that is an inference target acquired by imaging a test subject. Herein, for example, the supplementary information is information about a type of imaging apparatus, an imaging region, and an imaging condition. Various types of supplementary information will be described below.

In the supplementary information acquired by the supplementary information acquisition unit 101, an item describing the type of imaging apparatus is information indicating a type of medical image data imaging apparatus for generating medical image data that is an inference target. Examples of the type of medical image data imaging apparatus include the following.

Computed Radiography (CR) apparatus
Computed Tomography (CT) apparatus
Magnetic Resonance Imaging (MRI) apparatus
Positron Emission Tomography (PET) apparatus
Single Photon Emission Computed Tomography (SPECT) image data capturing apparatus
Ultrasound System (US) apparatus In the supplementary information acquired by the supplementary information acquisition unit 101, an item describing an imaging region is information indicating a region of a test subject imaged by the imaging apparatus. Specifically, the item describing an imaging region is information indicating a specific region such as a head region, a cervical region, a chest region, an abdominal region, a pelvic region, or four limbs, or information indicating a range such as an entire body or a thoracoabdominal region.

Further, in the supplementary information acquired by the supplementary information acquisition unit 101, an imaging condition is information including a plurality of items relating to conditions when imaging is executed, and examples thereof include use/non-use of a contrast medium, and a slice thickness. In addition, information about a condition unique to an imaging apparatus may be included in the imaging condition. For example, when a CT apparatus is used as the imaging apparatus for acquiring medical image data, information indicating a window level and a window width for displaying medical image data, such as a mediastinum condition and a lung field condition, may be included in the imaging condition. When an MRI apparatus is used as the imaging apparatus, information indicating an imaging sequence such as T1, T2, and FLAIR may be included in the imaging condition.

The inference model information acquisition unit 102 acquires information about an inference model from the database 105 connected thereto via the communication network 104. Herein, the information about the inference model is information relating to training data used for training the inference model, i.e., information about a disease name relating to a ground truth label which constitutes the training data and/or information about ground truth image data used for training the inference model. With respect to each of the inference models, model information and the above-described information about an inference model are stored in the database 105 in association with each other. Thus, the inference model information acquisition unit 102 can acquire the information at a desired timing. The model information about the inference model refers to information necessary for the inference model to perform inference. For example, the model information may be information about a network structure and a weight if the inference model employs an inference method using a neural network. In FIG. 1, although the database 105 is connected to the information processing apparatus 100 via the communication network 104, the configuration is not limited thereto. The database 105 can be any medium from which the information processing apparatus 100 can acquire information about the inference model. For example, the database 105 may be in a storage area of a hard disk physically associated with the information processing apparatus 100.

The inference model selection unit 103 receives a determination result from the inference model determination unit 106, and selects one inference model from a plurality of inference models based on the information about each of the inference models acquired by the inference model information acquisition unit 102.

Based on the supplementary information supplement to medical image data acquired by the inference model determination unit 106 and the information about inference models acquired by the inference model information acquisition unit 102, the inference model determination unit 106 determines whether each of the inference models is appropriate for performing inference on the medical image data that is an inference target, and transmits a determination result to the inference model selection unit 103.

Figure 2:
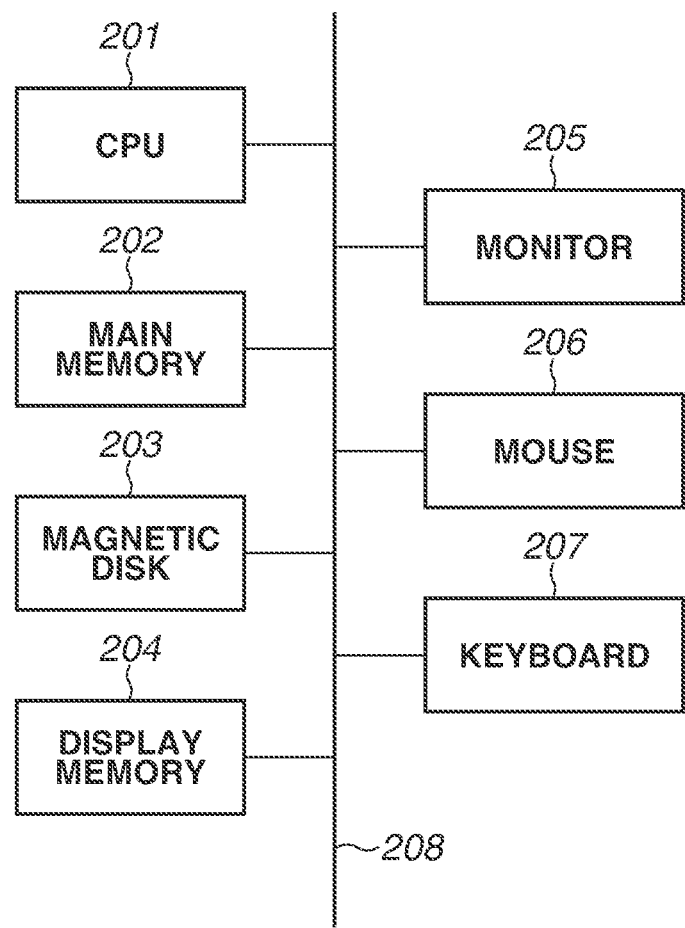
FIG. 2 is a block diagram illustrating a hardware configuration of the information processing apparatus.

FIG. 2 is a block diagram illustrating an example of a hardware configuration of the information processing apparatus 100. A central processing unit (CPU) 201 mainly controls operation of constituent elements. A main memory 202 stores a control program to be executed by the CPU 201, and provides a work area used when the CPU 201 executes the program. A magnetic disk 203 stores an operating system (OS), a device driver of a peripheral device, and programs for implementing various types of application software including a program for executing the processing described below. The CPU 201 executes the program stored in the main memory 202 or the magnetic disk 203, so that functions (software) of the information processing apparatus 100 illustrated in FIG. 1 and the processing illustrated in the below-described flowcharts are implemented.

A display memory 204 temporarily stores display data. A monitor 205 is, for example, a cathode-ray tube (CRT) monitor or a liquid crystal monitor which displays image data and text data based on the data stored in the display memory 204. A user executes input by pointing and input of characters via a mouse 206 and a keyboard 207, respectively. Each of the above-described constituent elements is communicably connected to each other via a common bus 208.

The CPU 201 is one example of a processor. The information processing apparatus 100 may include at least one of a graphics processing unit (GPU) and a field-programmable gate array (FPGA) in addition to the CPU 201. Alternatively, the information processing apparatus 100 may include at least one of the GPU and the FPGA instead of the CPU 201. Each of the main memory 202 and the magnetic disk 203 corresponds to an example of a memory.

Next, a processing procedure of the information processing apparatus 100 according to the present exemplary embodiment will be described with reference to FIG. 3.

In step S301, the supplementary information acquisition unit 101 acquires supplementary information supplement to medical image data that is an inference target. The supplementary information acquisition unit 101 acquires the supplementary information corresponding to the medical image data that is an inference target, for example, by using a Digital Imaging and Communications in Medicine (DICOM) header. It is specified that information corresponding to each item is to be described in the DICOM header in a form of a tag consisting of a pair of four-digit numbers. Thus, the supplementary information acquisition unit 101 can acquire the above-described supplementary information by referring to the information described in a predetermined tag. Specifically, a type of imaging apparatus is recorded in a tag (0008, 0060), and information about an examination region is recorded in a tag (0018, 0015). Further, information about a flow rate of a contrast medium is described in a tag (0018, 1046), and information about a period of flow of the contrast medium is described in a tag (0018, 1047). Thus, it is possible to determine whether the contrast medium is administered.

FIG. 4A illustrates an example of the supplementary information supplement to medical image data that is an inference target acquired by the supplementary information acquisition unit 101. The supplementary information is supplement to medical image data which has been acquired by a CT apparatus imaging a chest region of a test subject without administering the contrast medium. The supplementary information acquisition unit 101 can acquire the supplementary information not only from the DICOM header but also from a text file associated with the medical image data.

In step S302, the inference model information acquisition unit 102 acquires information about each inference model from the database 105. Examples of the information about each inference model acquired by the inference model information acquisition unit 102 are illustrated in FIG. 4B. The information about each inference model illustrated in FIG. 4B indicates information about training data used for training the inference model. For example, among pieces of information constituting the training data, a target disease name is information relating to a ground truth label, and the type of imaging apparatus, an imaging region, an imaging condition, use/non-use of a contrast medium, and a slice thickness are information relating to the ground truth image data. When the inference model is trained, for example, training data which consists of a pair of information relating to the ground truth label and information relating to the ground truth image data is used.

In step S303, the inference model selection unit 103 selects apiece of information about an inference model from among pieces of information about inference models in FIG. 4B acquired in step S302, and transmits the selected piece of information to the inference model determination unit 106.

In steps S304 to S306, based on the supplementary information supplement to the medical image data that is an inference target acquired in step S301 and the information about the inference model transmitted by the inference model selection unit 103 in step S303, the inference model determination unit 106 determines whether the inference model indicated by the information about the inference model is appropriate for performing inference on the medical image data that is an inference target.

First, in step S304, the inference model determination unit 106 compares the items constituting the information about the inference model with the items constituting the supplementary information, and determines whether information input to the item of the type of imaging apparatus of the information about the inference model matches information input to that of the supplementary information.

Next, in step S305, the inference model determination unit 106 determines whether information input to the item of the imaging region among the items constituting the information about the inference model matches information input to the item of the imaging region among the items constituting the supplementary information.

Then, in step S306, the inference model determination unit 106 determines whether information input to the item of the use/non-use of a contrast medium among the items constituting the information about the inference model matches information input to the item of the use/non-use of a contrast medium among the items constituting the supplementary information.

As described above, the inference model determination unit 106 sequentially determines whether information input to each of the items constituting the supplementary information of the medical image data that is an inference target match information input to each of the items constituting the information about the inference model. If all pieces of information input to the items match respective pieces of information input to the respective items (YES in step S306), the processing proceeds to step S307. If any one of the pieces of information input to the items does not match (NO in step S306), the processing proceeds to step S308. The inference model determination unit 106 may execute determination based on any one of the items of the type of imaging apparatus, the imaging region, and the use/non-use of the contrast medium, or may execute the determination based on an item selected by the user.

In step S307, the inference model determination unit 106 stores the information about the inference model transmitted by the inference model selection unit 103 in step S303 as a candidate to be output to the inference model selection unit 103.

In step S308, the inference model selection unit 103 determines whether there is information about an inference model on which the determination in steps S304 to S306 has not yet been executed. If the information exists (YES in step S308), the processing returns to step S303. If the information does not exist (NO in step S308), the processing proceeds to step S309.

In step S309, the inference model selection unit 103 acquires information about the inference model, which has been determined by the inference model determination unit 106 as having the pieces of information input to the items that match the pieces of information input to the items of the supplementary information in step S307, to select an inference model for performing inference on the medical image data that is an inference target from the plurality of inference models.

FIGS. 5A, 5B, and 5C illustrate an example of information about an inference model which completely matches the supplementary information of the medical image data that is an inference target and which is selected by the inference model selection unit 103 based on the supplementary information of the medical image data that is an inference target illustrated in FIG. 4A and the information about each inference model illustrated in FIG. 4B.

As described above, in the present exemplary embodiment, when a plurality of inference models is selectable, an inference model appropriate for the medical image data that is an inference target can be selected while reducing a load on the user.

<First Modification of First Exemplary Embodiment>

In the present exemplary embodiment, the inference model determination unit 106 determines whether the information input to the items of the type of imaging apparatus, the imaging region, and the use/non-use of a contrast medium of the supplementary information of the medical image data matches the information input to the items of the inference model. However, the information to be checked for determination is not limited to the above information. For example, the inference model determination unit 106 may also execute the determination by using another item of the supplementary information such as a slice thickness, a window level, or a window width, or the user may set in advance the information to be checked from among the pieces of information input to the items constituting the acquired supplementary information.

<Second Modification of First Exemplary Embodiment>

In the present exemplary embodiment, through the processing in steps S304 to S306, the inference model determination unit 106 determines whether the information input to the items constituting the supplementary information matches the information input to the items constituting the information about the inference model. However, a determination method is not limited to a method of determining whether the pieces of information input to the items of the supplementary information completely match the pieces of information input to the respective items of the information about the inference model.

In a case where information input to an item is character string information such as the information in the imaging region, for example, a map which indicates a specific character string as a match may be provided in advance, so that the inference model determination unit 106 can determine the match by referring to the map.

Specifically, FIG. 6 illustrates an example of the map to be referenced by the inference model determination unit 106 when the items to be compared by the inference model determination unit 106 is the item of the information about an imaging region. In the map in FIG. 6, a circle (o) mark indicates pieces of information determined to be conformable when the information in the item of the imaging region, which is one of the items constituting the supplementary information of the medical image data that is an inference target, is checked against the information in the item of the imaging region, which is one of the items constituting the information about the inference model.

For example, the inference model determination unit 106 refers to the map in FIG. 6 and determines that the supplementary information and the information about the inference model match in a case where "thoracoabdominal region" is the information input to the item of the imaging region, which is one of the items constituting the medical image data that is an inference target, and in a case where "chest region" or "abdominal region" is the information input to the item of the imaging region, which is one of the items constituting the information about the inference model. With this configuration, in a case where inference is to be performed on medical image data acquired by imaging a thoracoabdominal region, the inference model determination unit 106 can determine that information about an inference model with the imaging region of a chest region or an abdominal region matches the supplementary information. Thus, based on a determination result of the inference model determination unit 106, the inference model selection unit 103 can select an appropriate inference model from a plurality of inference models while saving time and effort of the user. A method which employs a map indicating a relationship between character strings is particularly effective to check information expressed in specific words, i.e., information in the item of the imaging region such as "chest region" or "abdominal region", with each other.

In a case where the inference model determination unit 106 determines a match between the items of the slice thickness or the window level and where the information input to the items is numerical information, a range of numerical values in which the inference model determination unit 106 determines as a match may be set in advance. For example, when information input to the item of the slice thickness, which is one of the items of the supplementary information of the medical image data that is an inference target is 3 mm, the inference model determination unit 106 determines that information in the item of the slice thickness matches if the information input in the item of the slice thickness, which is one of the items of the information about the inference model, is a value within a range of plus or minus 1 mm, i.e., 2 mm to 4 mm.

The inference model determination unit 106 may determine that the supplementary information and the information about the inference model match by a method different for each of the items, or a method specified depending on a type of information input to the item. Further, a map and conditions such as a threshold value and a range of numerical values that are set in advance to determine whether the information in the items match, may be set for each inference model.

In the first exemplary embodiment, the method has been described where the inference model determination unit 106 included in the inference model selection unit 103 checks the information input to each of the items constituting the supplementary information of the medical image data that is an inference target acquired by the supplementary information acquisition unit 101 against the information input to each of the items constituting the information about the inference model acquired by the inference model information acquisition unit 102. Then, if the information input to the items matches the information input to the respective items, the inference model selection unit 103 selects the inference model, the items of which have matched the respective items, as an inference model to be used for performing inference on the medical image data from the plurality of inference models.

In a second exemplary embodiment, a degree of matching between the items constituting the supplementary information of the medical image data that is an inference target and the items constituting the information about the inference model is calculated by the inference model determination unit 106. Then, based on the degree of matching, the inference model selection unit 103 selects an inference model used for performing inference on the medical image data that is an inference target. The inference model determination unit 106 applies a threshold value to the calculated degree of matching to determine whether the inference model is appropriate for the medical image data that is an inference target.

The processing procedure performed by the information processing apparatus 100 for determining whether the inference model is appropriate and for selecting an inference model to be applied to the medical image data that is an inference target from a plurality of inference models based on the determination result will be described with reference to FIG. 7.

Figure 3:
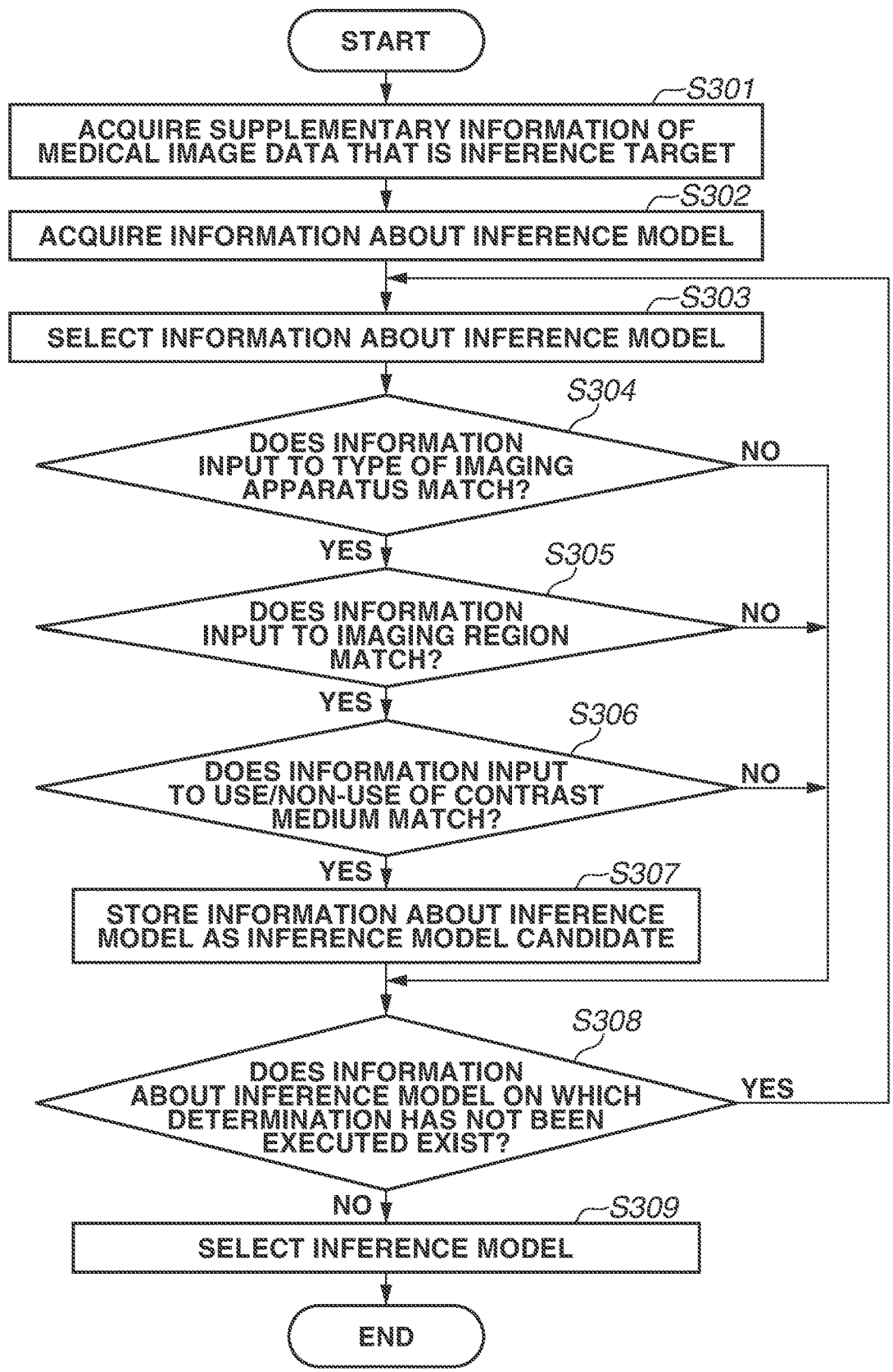
FIG. 3 is a flowchart illustrating processing according to the first exemplary embodiment.

The processing in steps S701, S702, and S703 is similar to the processing in steps S301, S302, and S303 of the flowchart in FIG. 3 according to the first exemplary embodiment. Thus, description thereof will be omitted.

In step S704, the inference model determination unit 106 calculates a degree of matching $r_{ij}$ (j=1, ..., n) with respect to each of the items, such as the items about a type of imaging apparatus and an imaging region, constituting the supplementary information and the information about the inference model. An index number allocated to each of the items is represented by "j", and the number of items is represented by "n". The degree of matching $r_{ij}$ of each of the items is calculated by the inference model determination unit 106. If the information input to the item completely matches that in the corresponding item, the degree of matching $r_{ij}$ is one ($r_{ij}$=1), and if the information in the item does not match that in the corresponding item, the degree of matching $r_{ij}$ is zero ($r_{ij}$=0). In a case where the information input to an item j is character string information, the inference model determination unit 106 may use a method described in the first exemplary embodiment as a degree of matching. In a case where numerical information is input to the item j, the inference model determination unit 106 may calculate an absolute value of a difference between numerical values input to the items and use the absolute value as the degree of matching. In the case where the degree of matching is calculated from the absolute value of the difference between the numerical values input to the items, the inference model determination unit 106 calculates the degree of matching $r_{ij}$ between the items based on a formula 1, where $x_j$ represents the numerical value of the item j of the supplementary information of the medical image data that is an inference target and $y_{ij}$ represents the numerical value of the item j of the information about an inference model i.

< Formula 1 >

$$r_{i,j} = 1 - \frac{|x_j - y_{ij}|}{\max - \min} \tag{1}$$

Herein, max represents a maximum value and min represents a minimum value of the numerical values $x_j$ and $y_{ij}$ (i=1, ..., N).

For example, a calculation method of a degree of matching of the item about a slice thickness executed by the inference model determination unit 106 will be described with respect to a case where 1.5 mm is input as the numerical information to the item about the slice thickness constituting the supplementary information of the medical image data that is an inference target.

For example, in a case where a plurality of inference models includes three inference models (i=1, 2, 3) and 1.0 mm, 1.5 mm, and 3.0 mm are information input to the respective items about the slice thickness constituting the information about each of inference models (i=1, 2, 3), the inference model determination unit 106 calculates the degree of matching for the items as r1j=0.75, r2j=0.00, and r3j=0.25, respectively.

In step S705, the inference model determination unit 106 calculates a degree of matching $R_i$ (i=1, ..., N) between the supplementary information of the medical image data that is an inference target and the information about the inference model. Herein, i represents an index number allocated to the inference model, and N represents the number of inference models. The degree of matching $R_i$ is calculated by obtaining a sum of the degrees of matching $r_{ij}$ (j=1, ..., n) of respective items j calculated by the inference model determination unit 106 in step S704.

< Formula 2 >

$$R_i = \frac{1}{n}\sum_{j=1}^{n} r_{ij} \tag{2}$$

FIGS. 8A, 8B, 8C, and 8D illustrate an example of a degree of matching of the inference model with the supplementary information. The inference model determination unit 106 calculates the degree of matching based on the formula 2 by using the supplementary information of the medical image data that is an inference target illustrated in FIG. 4A and the information about each inference model illustrated in FIG. 4B. FIG. 8C illustrates a result of calculation of the degree of matching for an item by the inference model determination unit 106. The degree of matching for the item about a slice thickness is calculated by the inference model determination unit 106 based on the formula 1. FIG. 8D illustrates a result of calculation of the degree of matching between the supplementary information supplement to the medical image data that is an inference target and the information about the inference model by the inference model determination unit 106 based on the formula 2 by using the result illustrated in FIG. 8C.

In step S706, the inference model determination unit 106 sets a threshold value to the degree of matching calculated as illustrated in FIG. 8D, and determines whether the inference model is appropriate for the input medical image data by determining whether the calculated degree of matching is the set threshold value or more. Then, based on a result of determination by the inference model determination unit 106, the inference model selection unit 103 selects an inference model for performing inference on the medical image data that is an inference target from the plurality of inference models.

The user can freely set the threshold value used by the inference model determination unit 106. For example, in a case where a threshold value is set to 0.7 with respect to the calculation result in FIG. 8D, the inference model determination unit 106 determines that the inference models 2 and 4 are appropriate for the medical image data that is an inference target.

The processing in steps S707, S708, and S709 is similar to the processing in steps S307, S308, and S309 according to the first exemplary embodiment. Thus, description thereof will be omitted.

As described above, in the present exemplary embodiment, the inference model determination unit 106 calculates a degree of matching between the supplementary information of medical image data that is an inference target and the information about an inference model, and applies a threshold value to the calculated degree of matching to determine whether the inference model indicated by the information about the inference model is appropriate for the medical image data that is an inference target. Therefore, the inference model selection unit 103 can flexibly select an inference model from a plurality of inference models for performing inference about diseases.

In the second exemplary embodiment, the method has been described where the inference model determination unit 106 calculates a degree of matching between the supplementary information and information about each inference model and applies a threshold value to the calculated degree of matching to determine whether the inference model indicated by the information about each inference model is appropriate for the medical image data that is an inference target.

In a third exemplary embodiment, a method is described where the inference model determination unit 106 calculates a degree of matching with consideration for priority of each item of the supplementary information. Then, based on the calculated degree of matching, the inference model selection unit 103 selects an inference model for performing inference on medical image data that is an inference target from a plurality of inference models. In the present exemplary embodiment, the inference model selection unit 103 sets a weight on each of the items, and selects an inference model based on the degree of matching for each of the items and the weight set thereto.

The processing procedure according to the present exemplary embodiment is similar to the processing procedure described in the second exemplary embodiment. However, in step S705, the degree of matching $R_i$ between the supplementary information of the medical image data that is an inference target and the information about the inference model is calculated by a different method.

In the present exemplary embodiment, when the degree of matching $R_i$ between the pieces of information is calculated, the inference model determination unit 106 sets a weight to each of the items j constituting the respective pieces of information and calculates a weighted sum. The inference model determination unit 106 sets a weight $w_j$ (j=1, ... , n) to each of the items j, and calculates the degree of matching $R_i$ between the pieces of information by the formula 3. The weight $w_j$ is set so that the sum becomes 1.

<Formula 3>

$$R_i = \sum_{j=1}^{n} w_j r_{ij} \quad (3)$$

For example, to the items such as a type of apparatus, an imaging region, use/non-use of a contrast medium, and a slice thickness, which constitute the pieces of information, the inference model determination unit 106 sets weights of 0.5, 0.2, 0.2, and 0.1, respectively (w=[0.5, 0.2, 0.2, 0.1]). FIGS. 9A, 9B, 9C, 9D, and 9E are diagrams illustrating an example of calculation of a degree of matching of each inference model based on the weights for the items set by the inference model determination unit 106 and the degree of matching of each item illustrated in FIG. 8C.

Similar to the processing in step S706 according to the second exemplary embodiment, the inference model determination unit 106 sets a threshold value to the calculated degree of matching between the pieces of information as illustrated in FIG. 9E, and determines whether the inference model indicated by the information about the inference model is appropriate for performing inference on the medical image data that is an inference target by determining whether the calculated degree of matching is the threshold value or more. In a case where a threshold value to be applied to the calculation result in FIG. 9E is set to 0.7, the inference model determination unit 106 determines that the inference models 2, 4, and 5 are appropriate for performing inference on the medical image data that is an inference target.

As described above, in the present exemplary embodiment, the inference model determination unit 106 calculates a degree of matching with consideration for priority of each item. Therefore, the inference model selection unit 103 can select an inference model to be applied to the medical image data that is an inference target from a plurality of inference models for performing inference about diseases depending on importance of the item.

In the first, the second, and the third exemplary embodiments, the method has been described where an appropriate inference model is selected by using the supplementary information of medical image data that is an inference target and the information about the inference model.

In a fourth exemplary embodiment, an supplementary information acquisition unit 1001 further acquires information about a test subject, and transmits the acquired information about the test subject to a disease estimation unit. Then, the disease estimation unit estimates a disease candidate based on the acquired information about the test subject, and an inference model selection unit 1003 selects an appropriate inference model from a plurality of inference models based on a result of estimation executed by the disease estimation unit.

First, a configuration of the present invention described in the present exemplary embodiment will be described with reference to FIG. 10. In addition to the configuration described in the first exemplary embodiment, an information processing apparatus 1000 includes a disease estimation unit 1005 for estimating a candidate of disease from the information about a test subject. The information processing apparatus 1000 is connected to a database 1007 and a medical information system 1008 via a communication network 1006. Herein, systems used at the hospital, such as a hospital information system (HIS) and an electronic health record system, are collectively called the medical information system 1008.

An inference model information acquisition unit 1002 is similar to that of the first exemplary embodiment, so that description thereof will be omitted.

The supplementary information acquisition unit 1001 which acquires supplementary information of medical image data that is an inference target further acquires test subject information from the medical information system 1008 connected thereto via the communication network 1006. Herein, for example, the test subject information acquired by the supplementary information acquisition unit 1001 refers to medical interview information or information described in the electronic health record. While the hospital information system and the electronic health record system are described as examples of the system from which the supplementary information acquisition unit 1001 acquires the test subject information, a system from which the information is acquired is not limited to the above as long as the test subject information can be acquired therefrom.

The disease estimation unit 1005 estimates a disease candidate based on the test subject information further acquired by the supplementary information acquisition unit 1001.

Based on the supplementary information of medical image data acquired by the supplementary information acquisition unit 1001, the information about the inference model acquired by the inference model information acquisition unit 1002, and the disease candidate acquired as a result of estimation executed by the disease estimation unit 1005, an inference model determination unit 1004 determines whether the inference model indicated by the information about the inference model is appropriate for performing inference on the medical image data that is an inference target.

The configuration of the information processing apparatus 1000 according to the fourth exemplary embodiment has been described as the above.

Figure 11:
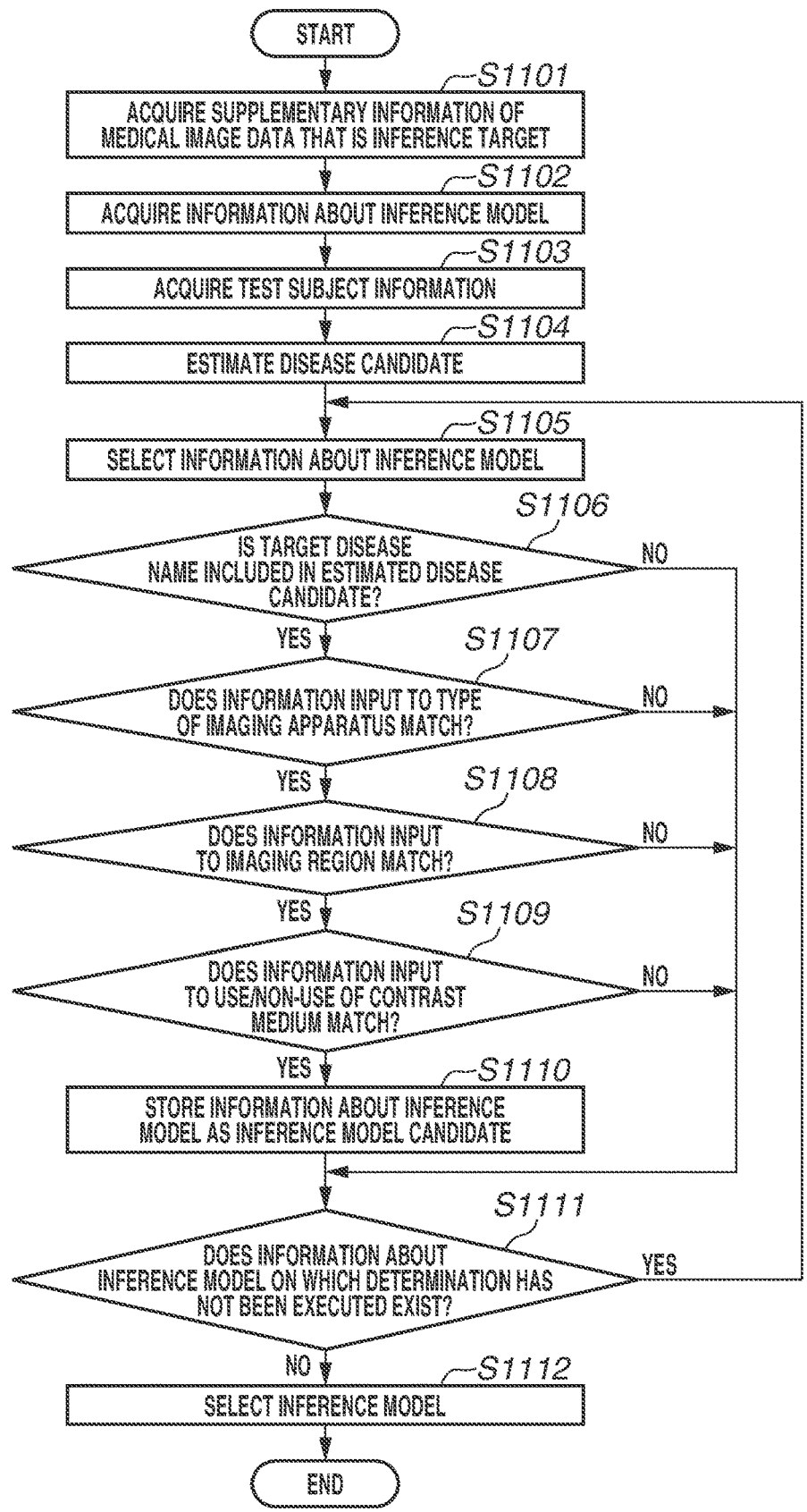
FIG. 11 is a flowchart illustrating processing according to the fourth exemplary embodiment.

Next, a processing procedure executed by the information processing apparatus 1000 according to the present exemplary embodiment will be described with reference to FIG. 11.

In step S1101, the supplementary information acquisition unit 1001 acquires supplementary information supplement to medical image data that is an inference target.

In step S1102, the processing up to acquisition of the information about each inference model by the inference model information acquisition unit 1002 is similar to the processing described in the first, the second, or the third exemplary embodiment.

In step S1103, the supplementary information acquisition unit 1001 further acquires the test subject information from the medical information system 1008. As the test subject information, the supplementary information acquisition unit 1001 acquires either medical interview information of the test subject or information in an electronic health record of the test subject or both from the medical information system 1008. Specifically, information such as a test subject name and a test subject ID are described in a DICOM header. The supplementary information acquisition unit 1001 makes an inquiry to a database of a system, such as the electronic health record system, that constitutes the medical information system 1008 using the above-described items to acquire information about the corresponding test subject.

In step S1104, a disease estimation unit 1105 estimates a disease candidate based on either the medical interview information or the information in the electronic health record that are the test subject information acquired by the supplementary information acquisition unit 1001 in step S1103 or both. In step S1104, as long as possible disease names are listed as the disease candidates as a result of estimation executed by the disease estimation unit 1105, a method of listing the disease names is not limited to the above-described method. For example, in a case where the test subject information acquired by the supplementary information acquisition unit 1001 is the medical interview information, the supplementary information acquisition unit 1001 may determine the disease candidates by checking a response to a question in the interview against a pre-registered rule, or may estimate the disease candidates using a known technique such as machine learning based on the response to the question. When the disease candidates are listed based on the rule, for example, estimation is executed in such a way that pneumothorax and aortic dissection are added to the disease candidates if symptoms include a chest pain. Further, when an electronic health record is acquired as the test subject information, information about past medical history is extracted and added to the disease candidates. Further, the disease estimation unit 1105 may add a possible complicating disease as a disease candidate by estimating the complicating disease from the past medical history by using a rule-based system such as a dictionary or machine learning. Through the above-described processing, as illustrated in FIG. 12A, information about the disease candidate estimated in step S1104 is added to the target disease name described in the supplementary information of the medical image data that is an inference target.

In step S1105, the inference model selection unit 1003 selects one piece of information from pieces of information about the inference models acquired in step S1102.

In step S1106, the inference model determination unit 1004 determines whether the target disease name described in the information about the inference model selected in step S1105 is included in the disease candidate estimated in step S1104. If the inference model determination unit 1004 determines that the target disease name is included (YES in step S1106), the processing proceeds to step S1107. If the inference model determination unit 1004 determines that the target disease name is not included (NO in step S1106), the processing proceeds to step S1111.

The processing in steps S1107 to S1112 is similar to the processing in steps S304 to S309 according to the first exemplary embodiment. Thus, description thereof will be omitted. In addition, the processing procedure in steps S1107 to S1112 may be replaced with the processing in steps S705 to S709 according to the second exemplary embodiment.

As described above, in the present exemplary embodiment, the supplementary information acquisition unit 1001 further acquires the information about a test subject, and the disease estimation unit 1005 estimates a disease candidate based on the information about the test subject, so that the inference model determination unit 1004 can determine whether an inference model is appropriate for performing inference on the medical image data that is an inference target. Further, based on a result of determination executed by the inference model determination unit 1004, the inference model selection unit 1003 can select an inference model appropriate for performing inference on the medical image data that is an inference target from a plurality of inference models.

Further, the present invention can also be realized by executing the following processing. Specifically, software (a program) that implements functions of the above-described exemplary embodiments is supplied to a system or an apparatus via a network or various storage media, and a computer (or a CPU or a micro-processing unit (MPU)) of the system or the apparatus reads and executes the program.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-115381, filed Jul. 3, 2020, which is hereby incorporated by reference herein in its entirety.

What is claimed is:

1. An information processing apparatus comprising:
at least one memory storing a program; and
at least one processor which, by executing the program, causes the information processing apparatus to:
acquire information about each inference model comprising a plurality of inference models;
acquire supplementary information supplement to medical image data that is an inference target acquired by imaging a test subject;
select an inference model to be applied to the medical image data from the plurality of inference models based on the information about each of the inference models and the supplementary information, wherein the medical image data is an inference target; and
calculate a degree of matching between at least one of items constituting the information about each of the inference models and at least one of items constituting the supplementary information supplement to the medical image data that is an inference target, and select the inference model to be applied to the medical image data that is an inference target based on the calculated degree of matching.

2. The information processing apparatus according to claim 1, wherein the information about each of the inference models acquired is information about training data used for training each of the inference models.

3. The information processing apparatus according to claim 2, wherein information is acquired about ground truth image data as the information about the training data.

4. The information processing apparatus according to claim 1, wherein the supplementary information and the information about each of the inference models are pieces of information each including at least one of a type of imaging apparatus, an imaging region, and an imaging condition.

5. The information processing apparatus according to claim 1, wherein a weight is set to each of the items, and selects the inference model based on the degree of matching between the items and the weight set to each of the items.

6. The information processing apparatus according to claim 2, further acquiring a disease name relating to a ground truth label as the information about the training data.

7. An information processing apparatus comprising:
at least one memory storing a program; and
at least one processor which, by executing the program, causes the information processing apparatus to:
acquire information about each inference model comprising a plurality of inference models;
acquire supplementary information supplement to medical image data that is an inference target acquired by imaging a test subject;
select an inference model to be applied to the medical image data from the plurality of inference models based on the information about each of the inference models and the supplementary information, wherein the medical image data is an inference target; and
estimate a disease name of the test subject,
wherein information about the test subject is acquired,
wherein the disease name of the test subject is estimated from the information about the test subject, and
wherein a disease candidate of the test subject is acquired as a result of estimation executed.

8. The information processing apparatus according to claim 7, wherein a degree of matching is calculated based on the disease name relating to the ground truth label acquired and the disease candidate of the test subject acquired, and select the inference model from the plurality of inference models based on the calculated degree of matching, wherein the selected inference model is to be applied to the medical image data.

9. The information processing apparatus according to claim 7, wherein the information about the test subject which is acquired is information including any one of information about medical interview of the test subject and information in an electronic health record.

10. An information processing method comprising:
acquiring information about each inference model comprising a plurality of inference models;
acquiring supplementary information supplement to medical image data that is an inference target acquired by imaging a test subject;
selecting an inference model to be applied to the medical image data from the plurality of inference models based on the information about each of the inference models and the supplementary information, wherein the medical image data is an inference target; and
calculating a degree of matching between at least one of items constituting the information about each of the inference models and at least one of items constituting the supplementary information supplement to the medical image data that is an inference target, and select the inference model to be applied to the medical image data that is an inference target based on the calculated degree of matching.

11. A non-transitory computer-readable storage medium storing a program for causing a computer to execute an information processing method comprising:
acquiring information about each inference model comprising a plurality of inference models;
acquiring supplementary information supplement to medical image data that is an inference target acquired by imaging a test subject;
selecting an inference model to be applied to the medical image data from the plurality of inference models based on the information about each of the inference models and the supplementary information, wherein the medical image data is an inference target; and
calculating a degree of matching between at least one of items constituting the information about each of the inference models and at least one of items constituting the supplementary information supplement to the mediinference model to be applied to the medical image data that is an inference target based on the calculated degree of matching.

* * * * *